United States Patent
Tegels

(10) Patent No.: US 9,358,077 B2
(45) Date of Patent: Jun. 7, 2016

(54) MARKERS FOR TISSUE TRACT DEPTH INDICATION AND METHODS

(71) Applicant: ST. JUDE MEDICAL PUERTO RICO LLC, Caguas, PR (US)

(72) Inventor: Zachary J. Tegels, Minneapolis, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 342 days.

(21) Appl. No.: 13/770,889

(22) Filed: Feb. 19, 2013

(65) Prior Publication Data
US 2013/0245644 A1 Sep. 19, 2013

(51) Int. Cl.
*A61B 17/04* (2006.01)
*A61B 19/00* (2006.01)
*A61B 17/00* (2006.01)

(52) U.S. Cl.
CPC ............ *A61B 19/46* (2013.01); *A61B 17/0057* (2013.01); *A61B 17/0469* (2013.01); *A61B 17/0482* (2013.01); *A61B 17/0485* (2013.01); *A61B 17/0487* (2013.01); *A61B 2017/00371* (2013.01); *A61B 2017/00663* (2013.01); *A61B 2017/0488* (2013.01)

(58) Field of Classification Search
CPC ........... A61B 17/0057; A61B 17/0469; A61B 17/0482; A61B 17/0485; A61B 19/46; A61B 2019/462; A61B 2017/0488
See application file for complete search history.

(56) References Cited

U.S. PATENT DOCUMENTS

| | | | |
|---|---|---|---|
| 3,470,875 A | 10/1969 | Johnson | |
| 5,431,666 A | 7/1995 | Sauer et al. | |
| 5,520,702 A | 5/1996 | Sauer et al. | |
| 5,562,686 A | 10/1996 | Sauer et al. | |
| 5,613,974 A | 3/1997 | Andreas et al. | |
| 5,643,292 A | 7/1997 | Hart | |

(Continued)

FOREIGN PATENT DOCUMENTS

| | | |
|---|---|---|
| EP | 0818178 A2 | 1/1998 |
| EP | 1158907 A1 | 12/2001 |

(Continued)

OTHER PUBLICATIONS

Notification of Transmittal of the International Search Report and the Written Opinion of the International Searching Authority, or the Declaration for International Application No. PCT/US2012/064768, mailed Feb. 19, 2013, (18 pp.).

(Continued)

*Primary Examiner* — Gregory Anderson
(74) *Attorney, Agent, or Firm* — Holland & Hart

(57) ABSTRACT

A vascular closure assembly configured to seal a puncture in a vessel that is accessible through a tissue tract. The vascular closure assembly includes a vascular closure device comprising a handle assembly, an insertion shaft, an anchor assembly, and at least one suture member. The insertion shaft extends distally from the handle assembly and carries a plurality of needles. The needles are operable to position at least one suture across the vessel puncture. The anchor assembly is positioned distal of the insertion shaft. The at least one suture member is positioned distal of the insertion shaft. The insertion shaft extends into the tissue tract to position the anchor assembly through the puncture and into the vessel and includes a first depth indicator on an outer surface thereof that indicates a depth of the tissue tract.

13 Claims, 14 Drawing Sheets

(56) References Cited

U.S. PATENT DOCUMENTS

| | | | |
|---|---|---|---|
| 5,674,231 | A | 10/1997 | Green et al. |
| 5,700,273 | A | 12/1997 | Buelna et al. |
| 5,709,692 | A | 1/1998 | Mollenauer et al. |
| 5,728,114 | A | 3/1998 | Evans et al. |
| 5,766,183 | A | 6/1998 | Sauer |
| 5,860,990 | A | 1/1999 | Nobles et al. |
| 5,972,005 | A | 10/1999 | Stalker et al. |
| 6,036,699 | A | 3/2000 | Andreas et al. |
| 6,048,357 | A | 4/2000 | Kontos |
| 6,059,800 | A | 5/2000 | Hart et al. |
| 6,068,648 | A * | 5/2000 | Cole ................. A61B 17/0401 606/144 |
| 6,136,010 | A | 10/2000 | Modesitt et al. |
| 6,355,050 | B1 | 3/2002 | Andreas et al. |
| 6,562,052 | B2 | 5/2003 | Nobles et al. |
| 6,623,509 | B2 | 9/2003 | Ginn |
| 6,641,592 | B1 | 11/2003 | Sauer et al. |
| 6,896,692 | B2 | 5/2005 | Ginn et al. |
| 6,911,034 | B2 | 6/2005 | Nobles et al. |
| 6,932,824 | B1 | 8/2005 | Roop et al. |
| 6,964,668 | B2 | 11/2005 | Modesitt et al. |
| 6,969,397 | B2 | 11/2005 | Ginn |
| 7,001,400 | B1 | 2/2006 | Modesitt et al. |
| 7,083,635 | B2 | 8/2006 | Ginn |
| 7,235,087 | B2 | 6/2007 | Modesitt et al. |
| 7,361,183 | B2 | 4/2008 | Ginn |
| 7,390,328 | B2 | 6/2008 | Modesitt |
| 7,553,319 | B2 | 6/2009 | Bagaoisan et al. |
| 7,601,161 | B1 | 10/2009 | Nobles et al. |
| 7,621,937 | B2 | 11/2009 | Pipenhagen et al. |
| 7,686,821 | B2 | 3/2010 | Hathaway et al. |
| 7,731,726 | B2 | 6/2010 | Belhe et al. |
| 7,744,610 | B2 | 6/2010 | Hausen |
| 7,752,853 | B2 | 7/2010 | Singh et al. |
| 7,753,933 | B2 | 7/2010 | Ginn et al. |
| 7,837,696 | B2 | 11/2010 | Modesitt et al. |
| 7,842,047 | B2 | 11/2010 | Modesitt et al. |
| 7,842,048 | B2 | 11/2010 | Ma |
| 7,846,170 | B2 | 12/2010 | Modesitt et al. |
| 7,850,701 | B2 | 12/2010 | Modesitt et al. |
| 7,883,517 | B2 | 2/2011 | Pantages et al. |
| 7,985,240 | B2 | 7/2011 | Bagaoisan et al. |
| 8,029,476 | B2 | 10/2011 | Rosenberg et al. |
| 8,048,092 | B2 | 11/2011 | Modesitt et al. |
| 8,083,768 | B2 | 12/2011 | Ginn et al. |
| 8,192,456 | B2 | 6/2012 | Holman et al. |
| 2005/0085854 | A1 | 4/2005 | Ginn |
| 2006/0212071 | A1 | 9/2006 | Ginn et al. |
| 2008/0065151 | A1 | 3/2008 | Ginn |
| 2009/0099578 | A1 | 4/2009 | Heneveld et al. |
| 2009/0306685 | A1 | 12/2009 | Fill |
| 2010/0042118 | A1 | 2/2010 | Garrison et al. |
| 2011/0071567 | A1 | 3/2011 | Modesitt et al. |

FOREIGN PATENT DOCUMENTS

| | | | |
|---|---|---|---|
| EP | 1327419 | A2 | 7/2003 |
| EP | 1349501 | A2 | 10/2003 |
| EP | 1677682 | A2 | 7/2006 |
| EP | 1972282 | A2 | 9/2008 |
| EP | 2147640 | A2 | 1/2010 |
| EP | 2298180 | A1 | 3/2011 |
| WO | 9703613 | A1 | 2/1997 |
| WO | 0051498 | | 9/2000 |
| WO | 0078226 | A1 | 12/2000 |
| WO | 2010081106 | A1 | 7/2010 |

OTHER PUBLICATIONS

Notification of Transmittal of the International Search Report and the Written Opinion of the International Searching Authority, or the Declaration for International Application No. PCT/US2012/066012, mailed Feb. 19, 2013, (17 pp.).

Notification of Transmittal of the International Search Report and the Written Opinion of the International Searching Authority, or the Declaration for International Application No. PCT/US2012/064770, mailed Feb. 19, 2013, (16 pp.).

PCT Communication Relating to the Results of the Partial International Search for International Application No. PCT/US2012/041196, mailed Sep. 11, 2012.

McCrea et al., U.S. Appl. No. 61/494,345, filed Jun. 7, 2011.

Halac et al., U.S. Appl. No. 61/487,633, filed May 18, 2011.

\* cited by examiner

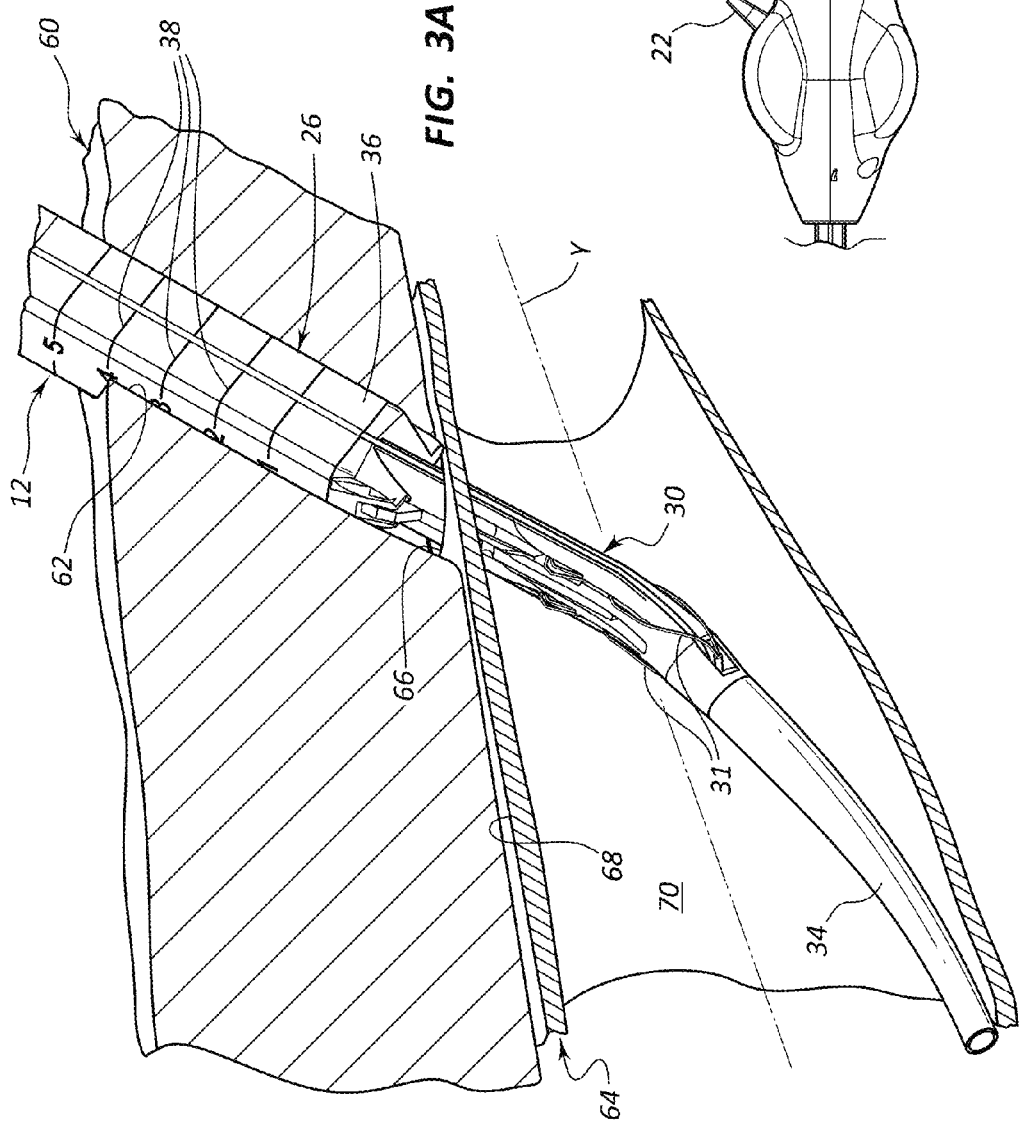

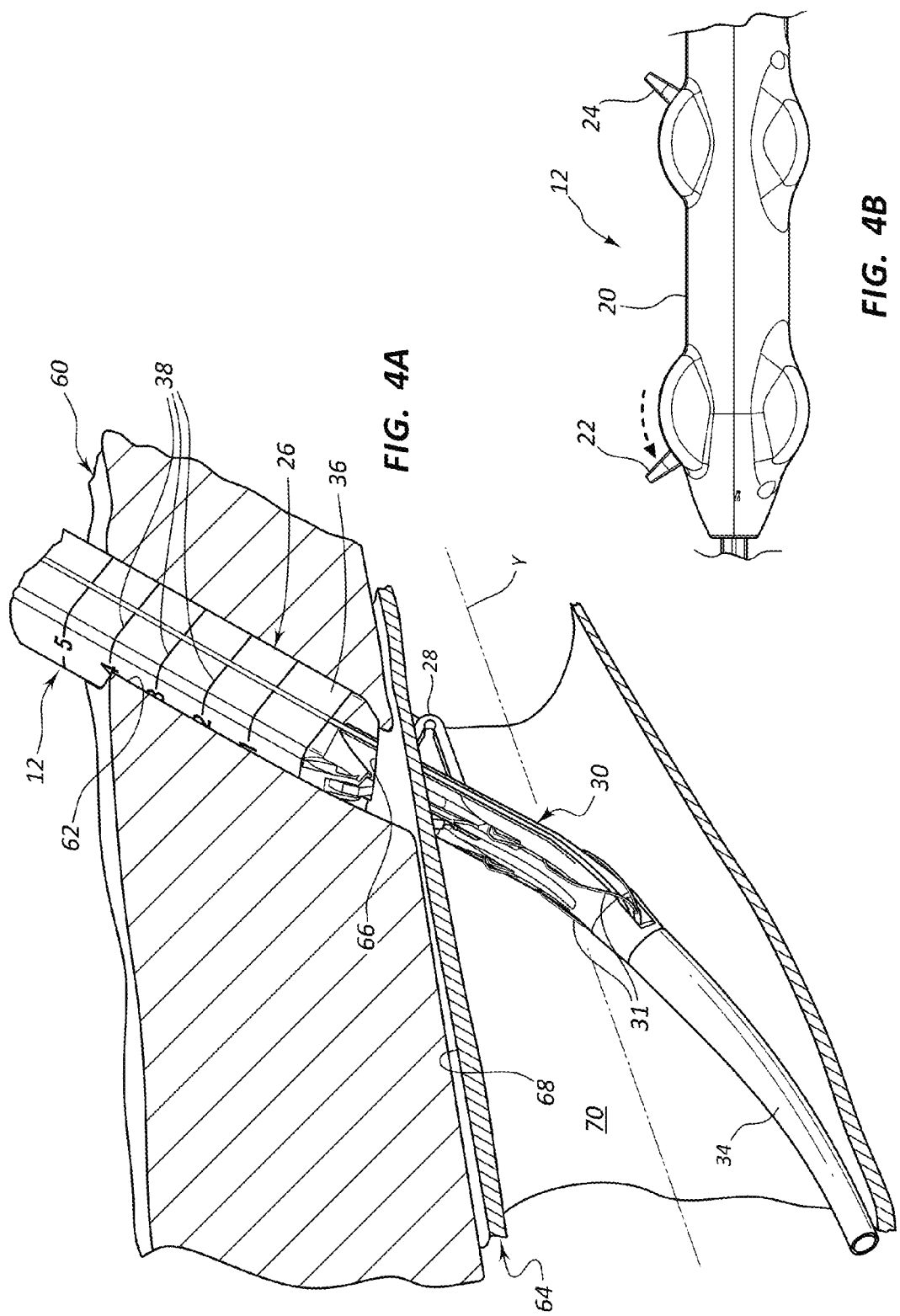

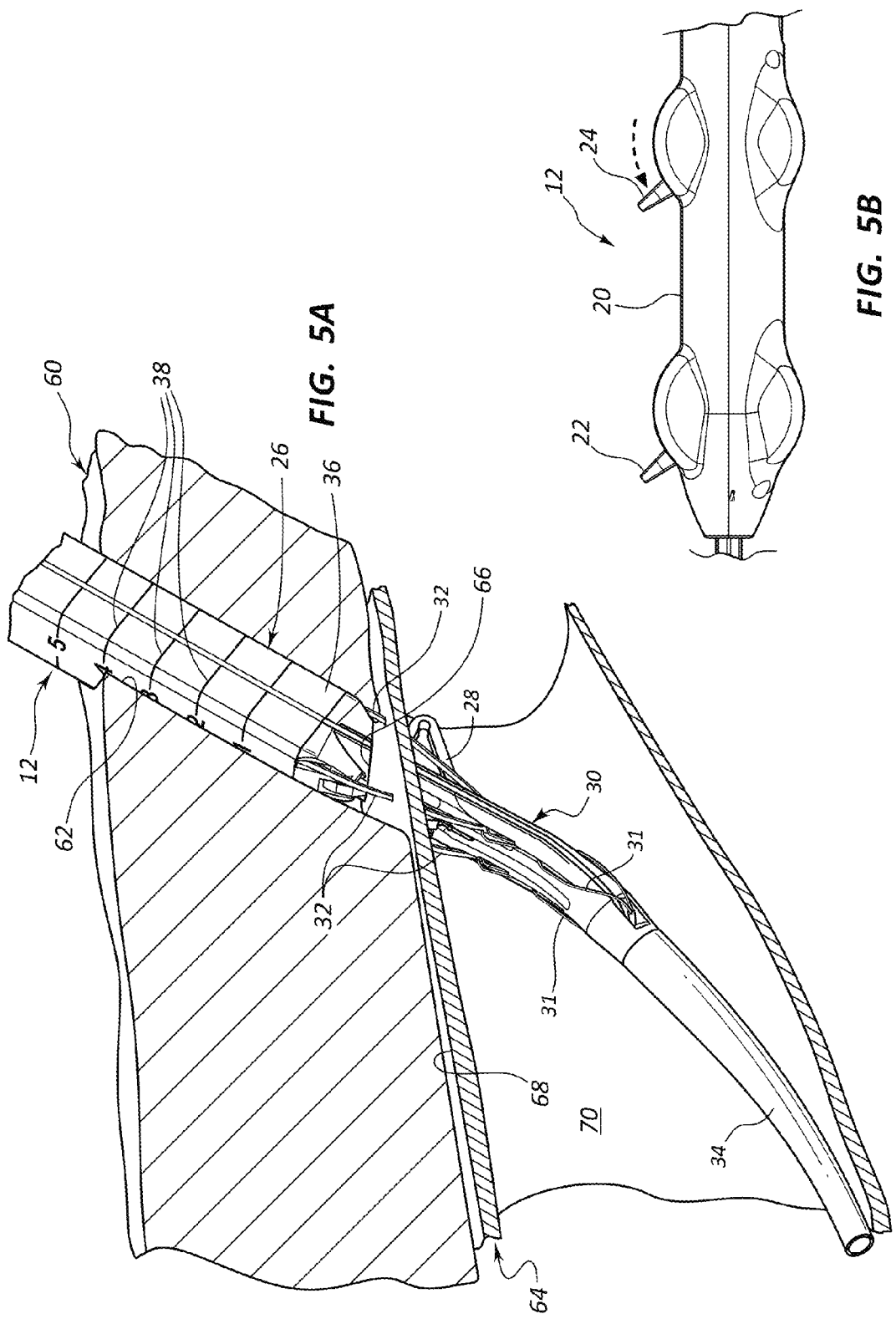

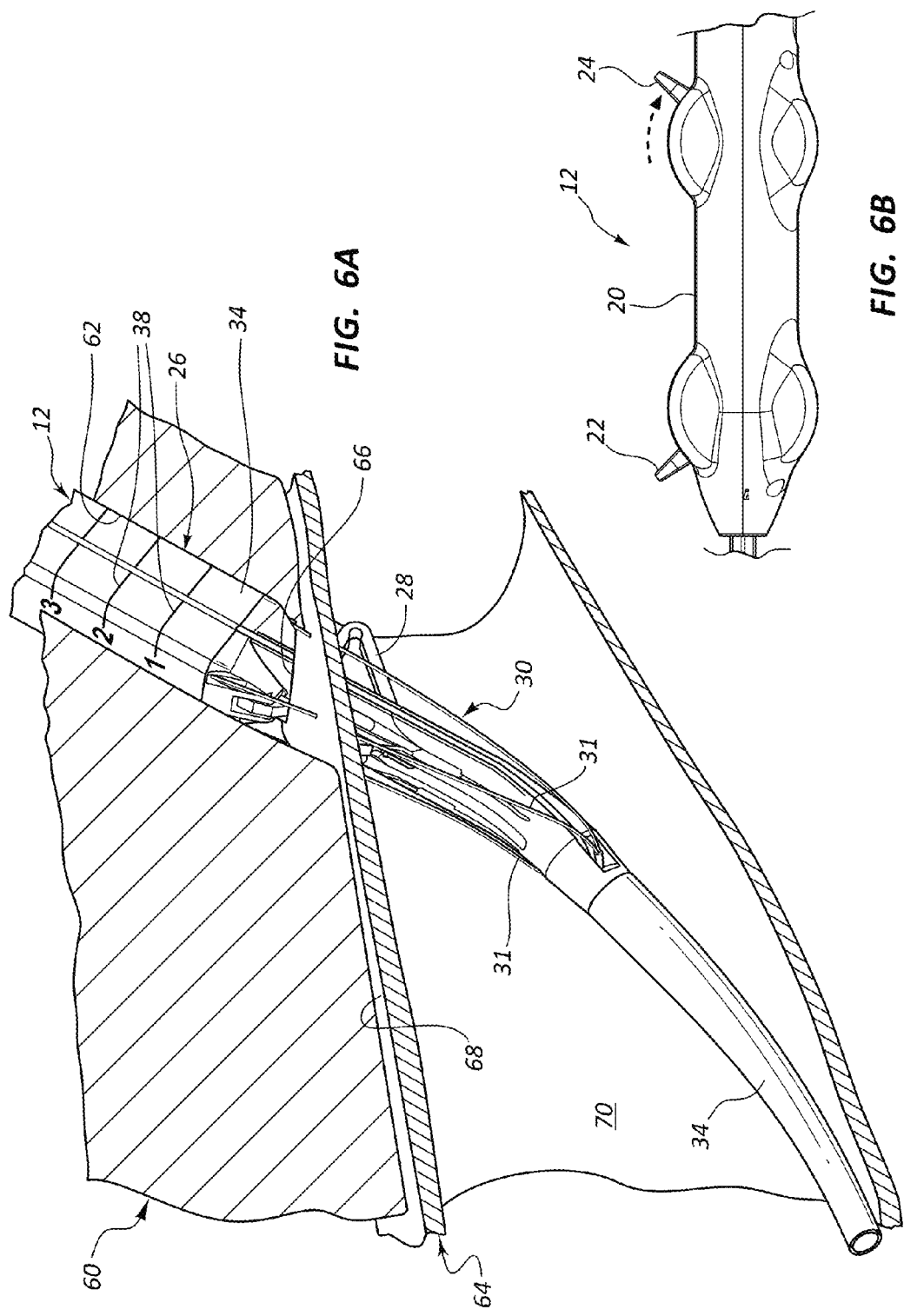

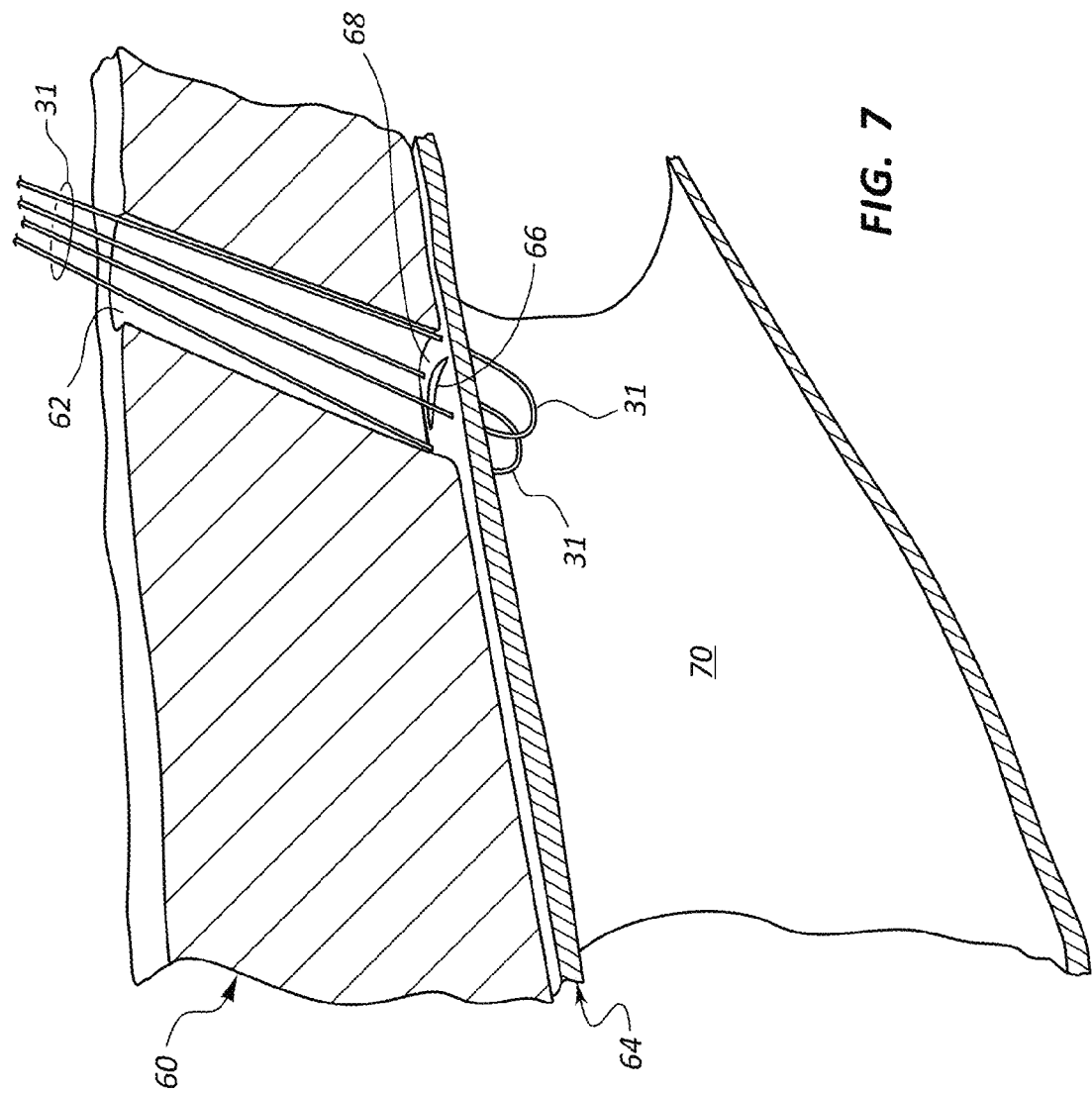

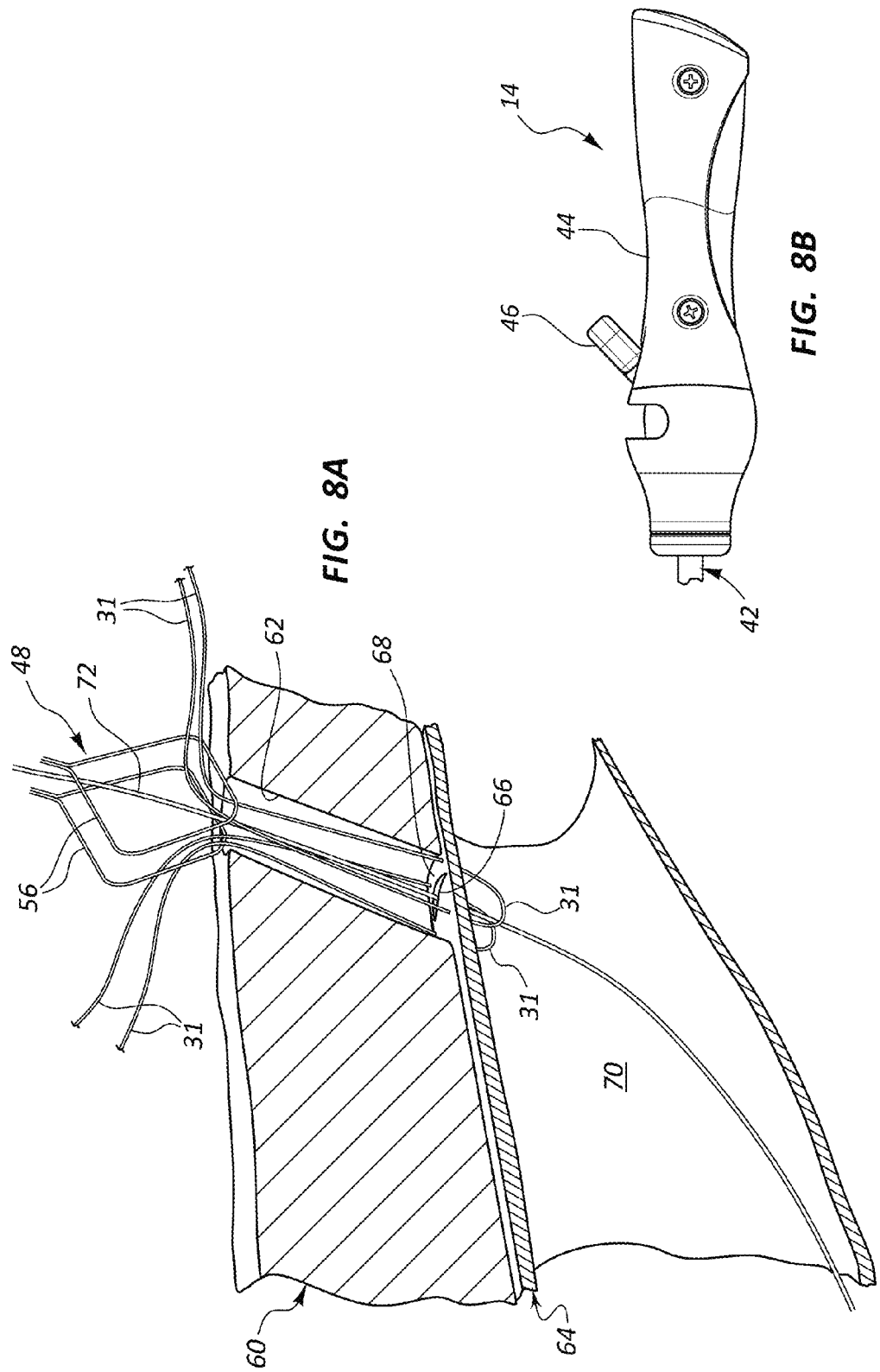

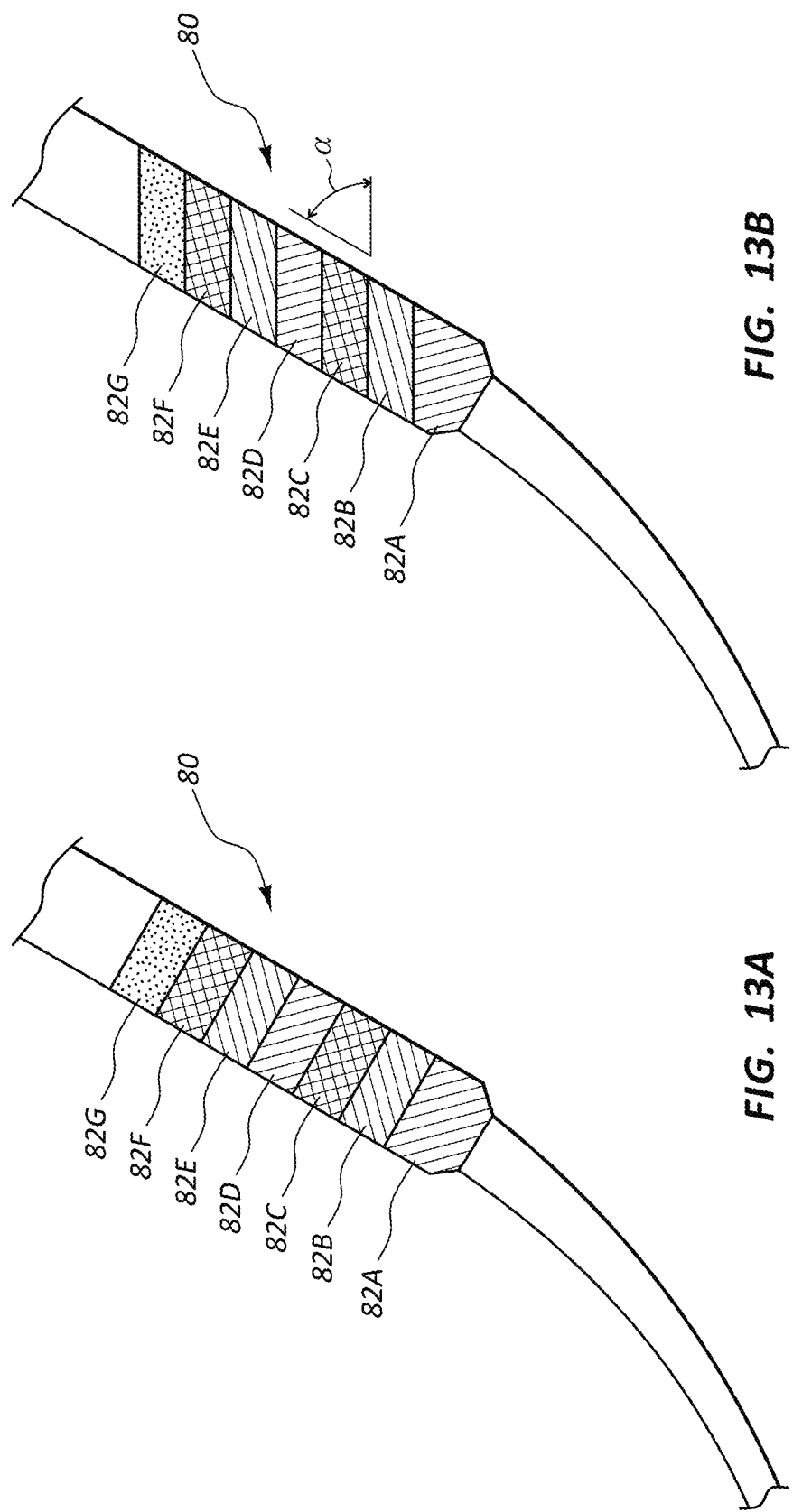

MARKERS FOR TISSUE TRACT DEPTH INDICATION AND METHODS

CROSS-REFERENCE TO RELATED APPLICATION

This application claims the benefit of the filing date of U.S. Provisional Application No. 61/610,942, filed 14 Mar. 2012, and entitled MARKERS FOR TISSUE TRACT DEPTH INDICATION AND METHODS, the disclosure of which is incorporated, in its entirety, by this reference.

TECHNICAL FIELD

The present disclosure relates to closure devices, and more specifically relates to tissue tract depth indicators for vascular closure assemblies.

BACKGROUND

Various medical procedures, particularly cardiology procedures, involve accessing a corporeal vessel through a percutaneous sheath. The sheath necessarily requires the formation of a hole or opening in the vessel wall so that a medical procedure can be performed via the sheath. After the particular medical procedure has been performed, the sheath must eventually be removed from the vessel and the access hole in the vessel wall must be closed.

A number of prior vascular closure devices have been developed in attempting to provide a solution for the problem of closing a hole in the vessel wall. Tissue approximation typically involves passing a length of suture into and through adjacent vessel and subcutaneous tissue, across the vessel opening, and back into and through adjacent vessel and subcutaneous tissue. Certain prior closure devices have involved relatively complicated methods and devices for extracting a length of suture from inside the vessel so that the physician can approximate tissue surrounding the hole in the vessel wall through use of the suture.

After the suture has been placed across a hole in the vessel and the treatment of the patient through the hole is completed, the suture may be used to seal the hole. Various devices such as suture locking devices, suture knot placement devices, and suture cutting devices may be used as part of a procedure to seal the hole using the suture. These devices are delivered to the hole by access through a layer of subcutaneous tissue, the thickness of which may vary between patients. Proper sealing of the hole using the suture is often dependent on accurate positioning of these devices within the subcutaneous tissue.

SUMMARY

One aspect of the present disclosure relates to a vascular closure assembly configured to seal a puncture in a vessel accessible through a tissue tract. The vascular closure assembly includes a vascular closure device comprising a handle assembly, an insertion shaft, an anchor assembly, and at least one suture member. The insertion shaft extends distally from the handle assembly and carries a plurality of needles. The needles are operable to position at least one suture across the vessel puncture. The anchor assembly is positioned distal of the insertion shaft. The at least one suture member is positioned distal of the insertion shaft. The insertion shaft extends into the tissue tract to position the anchor assembly through the puncture and into the vessel, and includes a first depth indicator on an outer surface thereof that indicates a depth of the tissue tract.

The vascular closure assembly includes at least one of a suture cutting device and a suture locking device that each includes a suture handle portion and a carrier member. The carrier member extends distally from the suture handle portion and into the tissue tract during operation. The carrier member includes a second depth indicator on an outer surface thereof that indicates the depth of the tissue tract.

The first and second depth indicators may be identical. The first and second depth indicators may each include a plurality of patterns. The first and second depth indicators may each include a plurality of colors. The first and second depth indicators may include a plurality of indices. The first depth indicator may be activated by contact with the tissue tract. The first depth indicator may be actuated manually.

Another aspect of the present disclosure relates to a method of closing a vessel puncture accessible through a tissue tract. The method includes providing a suture positioning device and a suture securing device, wherein the suture positioning device comprises a first handle portion, an insertion member, and an anchor assembly, and the suture securing device comprising a second handle portion and a carrier member. The method also includes inserting the anchor assembly through the vessel puncture and the insertion member into the tissue tract, positioning at least one suture across the vessel puncture with the suture positioning device, providing a first visual indicator on the insertion shaft of a depth of the tissue tract, identifying a second visual indicator on the carrier member that represents the depth of the tissue tract, and inserting the carrier member into the tissue tract to the depth while observing the second visual indicator.

At least one of the first and second visual indicators may include at least one pattern. At least one of the first and second visual indicators may include a plurality of colors. The suture positioning device may include a plurality of needles, and the method further includes advancing and retracting the plurality of needles to position the suture across the vessel puncture. The suture securing device may include a suture cutter configured to cut the suture within the tissue tract. The suture securing device may include a suture locking device configured to position a suture lock on the suture to maintain tension in the suture.

A further aspect of the present disclosure relates to a tissue puncture closure device that includes a first portion insertable through a tissue tract to a tissue puncture, and a second portion positioned outside of the tissue tract and configured to control operation of the first portion. The first portion includes a tissue depth indicator configured to measure a depth of the tissue tract.

The tissue depth indicator may include a plurality of colors along a length of the first portion. The tissue depth indicator may include a plurality of patterns along a length of the first portion. The tissue depth indicator may be automatically activated upon contact with the tissue tract. The tissue depth indicator may change colors upon contact with the tissue tract. The tissue depth indicator may be mechanically activated by operation of the second portion.

The foregoing and other features, utilities, and advantages of the invention will be apparent from the following detailed description of the invention with reference to the accompanying drawings.

BRIEF DESCRIPTION OF THE DRAWINGS

FIG. 3A shows the suture placement device of FIG. 1 inserted through a tissue tract and vessel puncture and into a vessel.

FIG. 3B shows a handle of the suture placement device of FIG. 3A in a first operation position.

FIG. 4A shows an anchor assembly of the suture placement device of FIG. 3A in a deployed position.

FIG. 4B shows the handle of the suture placement device of FIG. 4A in a second operation position.

FIG. 5A shows the suture placement device of FIG. 4A with needles extending through the vessel wall.

FIG. 5B shows the handle of the suture placement device of FIG. 5A in a third operation position.

FIG. 6A shows the suture placement device of FIG. 5A with the needles retracted to draw sutures through the vessel wall.

FIG. 6B shows the handle of the suture placement device of FIG. 6A in a fourth operation position.

FIG. 7 shows a vessel with the suture placement device removed and sutures placed across the vessel puncture.

FIG. 8A shows the sutures of FIG. 7 routed through snares of the suture locking device of FIG. 1.

FIG. 8B shows the handle of the suture locking device of FIG. 8A in a first operation position.

FIG. 13A shows an example marking pattern for a vascular closure system.

FIG. 13B shows another example marking pattern for a vascular closure system.

DETAILED DESCRIPTION

Figure 1:
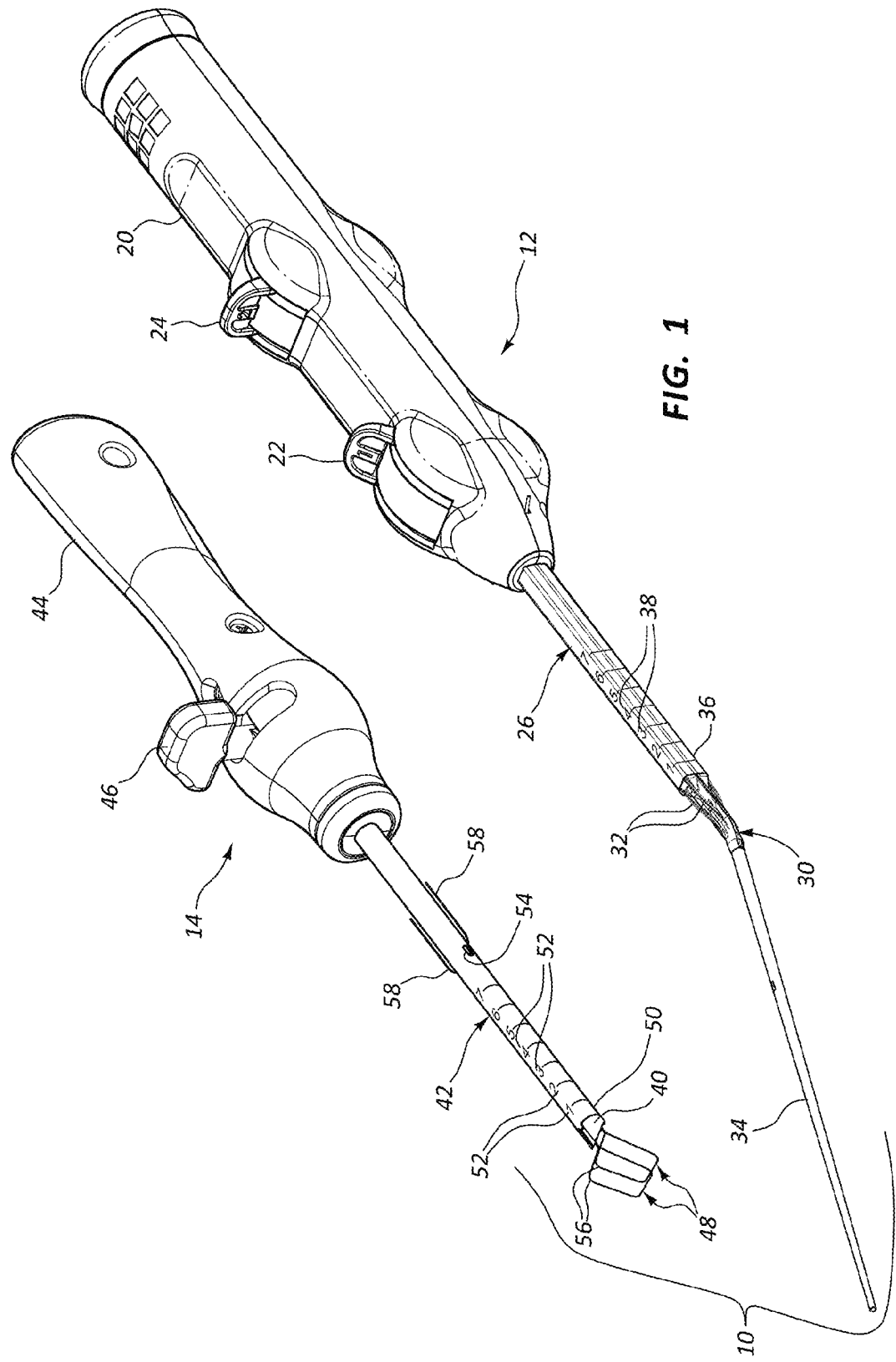
FIG. 1 is a perspective view of an example vascular closure system having a suture placement device and a suture locking device in accordance with the present disclosure.

The present disclosure is directed to a marking system used with devices that place at least one suture across a wound (e.g., a puncture in a vessel) and use the at least one suture to seal the wound. The marking system provides a visual indication to the operator of an insertion depth for the devices into a percutaneous incision leading to the wound. In one embodiment, one of the devices is adapted and configured to place a pair of sutures across an opening in a wall of the vessel. The device is inserted into the percutaneous incision a certain depth where the device deploys the sutures across the vessel opening by inserting a plurality of needles through the vessel wall adjacent to the opening. The needles grasp lengths of suture held by the device within the vessel, and withdrawing the needles pulls the lengths of suture through the vessel wall. The sutures may be subsequently used to close the opening using other devices that are also inserted into the percutaneous incision.

In one example, the percutaneous incision includes a tissue tract formed through a layer of skin, fat, or muscle. The vessel wall is accessible subcutaneously through the tissue tract. A depth of the tissue tract may vary for each patient. For example, relatively healthy patients with a low body fat content may have a shallow tissue tract, while obese patients may have a deep tissue tract. Determining the depth and other aspects of the tissue tract may be helpful in the original placement of sutures across the vessel puncture and later use of the sutures to help seal the vessel puncture.

One aspect of the present disclosure relates to the use of depth indicators or markings on the devices inserted through the tissue tract to perform procedures at the vessel puncture. The markings may be used on the suture placement device to help determine a depth of the tissue tract as part of operating the suture placement device to place a suture across the vessel puncture. Once the depth of the tissue tract is known using these markings, the depth information may be used while operating secondary devices (e.g., a suture cutting device, suture knot placement device, or suture locking device) in a subsequent operational procedure to seal the vessel opening.

In one example, the same or similar markings used for the suture placement device to determine a depth of the tissue tract may be used on the secondary devices (e.g., the suture cutting device, suture knot placement device, or suture locking device). Various markings may be used as a visual indicator to the operator. For example, the markings may comprise different marking patterns positioned along a length of that portion of the suture placement device that is inserted into the tissue tract. Other example markings include numerical markings, different sized or shaped markings, or different marking locations around a circumference of that portion of the suture placement device that is inserted into the tissue tract. Other marking examples may include materials that change color or sheen upon contact with tissue. The contact with tissue may change a temperature of the material, may create a chemical reaction, or induce a change that results in a visual indication to the operator that that portion of the suture placement device has been positioned within the tissue tract.

In one application, an insertion shaft portion of a suture placement device includes a plurality of markers along its length on an exterior surface thereof. The markers indicate to the operator a depth of the tissue tract measured from an outer skin surface of the patient to the vessel puncture. The depth of the tissue tract is then used by the operator when inserting a suture locking device (or other secondary device) along the sutures to be placed at an exterior surface of the vessel near the vessel puncture. Because the operator knows the depth of the tissue tract, if the suture locking device is not inserted to that same depth before the operator receives tactile feedback that the suture locking device has reached the vessel wall, the operator has some indication that the suture locking device has hit an obstruction or other complication that prevents insertion to a proper depth.

Figure 2:
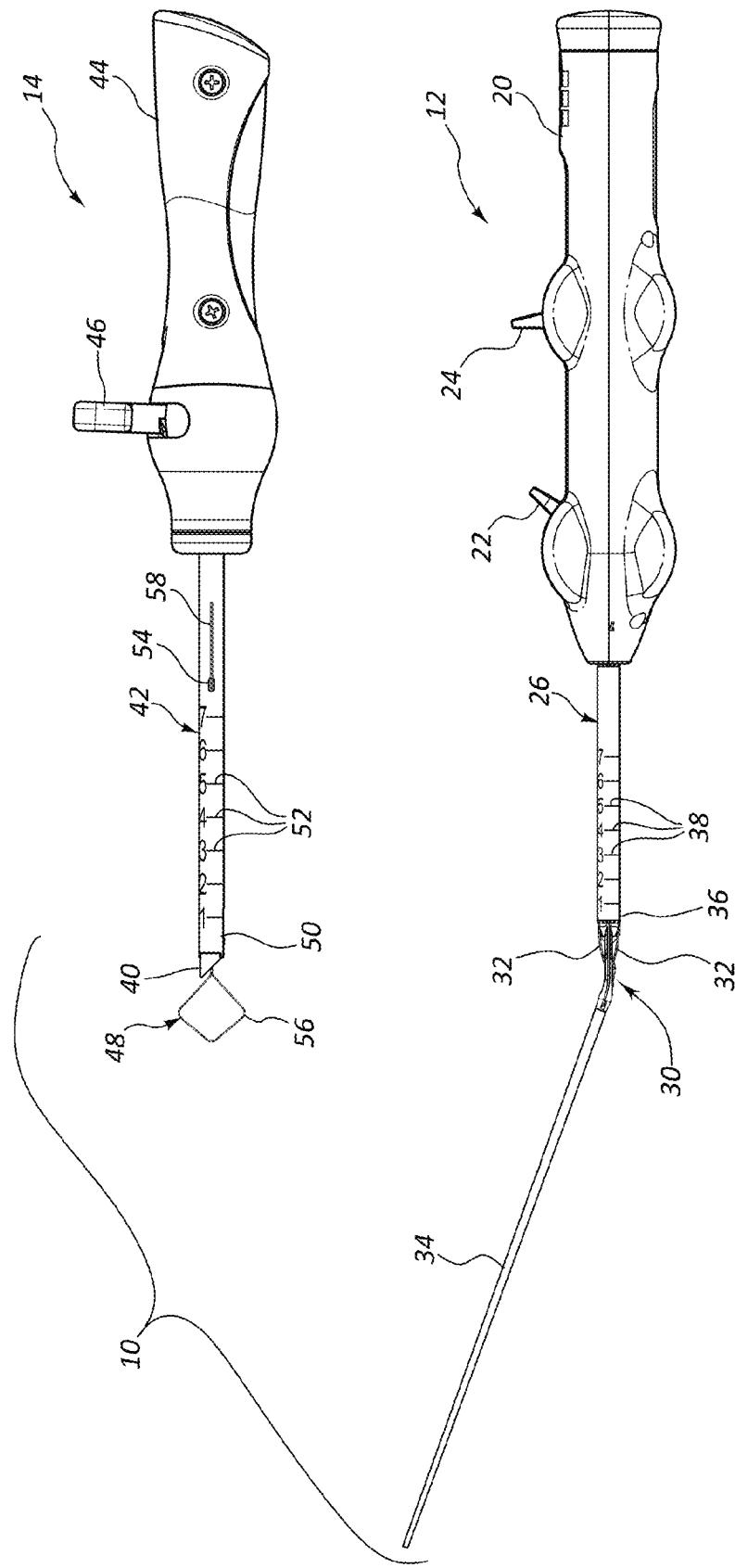
FIG. 2 is a side view of the vascular closure system of FIG. 1.

Referring now to FIGS. 1 and 2, an example vascular closure system 10 is shown and described. The vascular closure system 10 includes a suture placement device 12 and a suture locking device 14. The suture placement device 12 is operable to position at least one suture at a vessel puncture. For example, the suture may be advanced through a wall of the vessel adjacent to the vessel puncture. Some types of suture placement devices 12 may be configured to advance a single suture through the vessel wall at spaced apart locations adjacent to the vessel puncture. Other types of suture placement devices 12 may position multiple sutures at the vessel puncture (e.g., placing multiple sutures through the vessel wall).

The suture locking device 14 may be used to position a locking assembly at the vessel puncture that maintains tension in the suture. The locking assembly carried by the suture locking device may be operable to lock one or more sutures (e.g., lock two sutures) that each include two free ends extending through the vessel wall. Other types of suture-related devices may be used in place of the suture locking device 14 as part of the vascular closure system 10. For example, a suture knot tying device may be used to advance a knot along a length of the suture that has been positioned across the vessel puncture using the suture placement device 12. The suture knot placement device may advance the knot along the suture to the vessel puncture to help maintain tension in the suture to hold closed the vessel puncture.

Another device that may be used in place of the suture locking device 14 is a suture cutting device. The suture cutting device may be advanced along the suture to a location adjacent to the vessel puncture such as, for example, at a location proximal of a knot that has been advanced along the suture to the vessel puncture.

Any of the devices used with the suture placement device 12, whether a suture locking device, a suture knot placing device, a suture cutting device, or any other device used independent of the suture placement device 12 that is insertable through the tissue tract to the vessel puncture, the operator typically can benefit from knowing a depth of the tissue tract that must be navigated to obtain access to the vessel puncture. One aspect of the present disclosure utilizes markings on the suture placement device 12 to help determine a depth of the tissue tract during operation of the suture placement device 12. This tissue tract depth, as determined using the markings, may be used with the secondary device (e.g., the suture locking device 14) so that the operator has a visual indication in addition to the tactile responses of the device during use to help determine proper depth and placement relative to the vessel puncture.

The suture placement device 12 includes a handle 20, first and second actuators 22, 24, a handle 20, an insertion shaft 26, an anchor 28, a suture carrying portion 30, a plurality of needles 32, and a distal locator tip 34. Operating the first actuator 22 moves the anchor 28 between a retracted position (see FIG. 1) and an extended or expanded position (see FIG. 4A). Operating the anchor 28 into the expanded position may also concurrently capture a portion of the vessel wall between the insertion shaft 26 and the anchor 28. This captured portion of the vessel wall may be arranged substantially perpendicular to an axial length of the suture placement device 12. Operating the second actuator 24 moves the needles longitudinally between a withdrawn position (see FIG. 1) and an advanced position (see FIG. 5A). Operating the needles 32 may advance the needles distally through the vessel wall where the needles capture sutures 31 carried by the suture carrying portion 30. Operating the needles 32 in a proximal or withdrawn direction draws the sutures 31 through the vessel wall (see FIG. 6A). Further details concerning operation of suture placement device 12 are shown and described with reference to U.S. Patent Application No. 61/494,345 filed on 7 Jun. 2011, and entitled "Large Bore Closure Device and Methods," which is incorporated herein in its entirety by this reference.

The insertion shaft 26 may include a distal end 36 and a plurality of first markings 38. The first markings 38 may be spaced apart incrementally from the distal end 36 towards the handle 20. The first markings 38 may include a numerical figure aligned with a linear marking that extends around at least a portion of a circumference of the insertion shaft 26. The first markings 38 may be spaced apart axially a predetermined distance from each other such as, for example, 1 mm or ⅛ inch. The first markings 38 may provide a visual indication to the operator of a depth of the tissue tract through which the suture placement device 12 is inserted to gain access to the vessel puncture.

Referring to FIGS. 3A-7, operation of the suture placement device 12 relative to a patient is described. FIG. 3A shows the suture placement device 12 inserted through a tissue tract 62 of a tissue layer 60 and through a vessel puncture 66 of a vessel 64 into a vessel interior 70. The distal end 36 of the insertion shaft 26 is typically abutted against an outer surface 68 of the vessel 64. The first and second actuators 22, 24 shown in FIG. 3B are maintained in a first operated position prior to expanding the anchor and advancing the needles.

Referring now to FIGS. 4A and 4B, the first actuator 22 is operated to expand the anchor 28. The anchor 28 may capture a portion of the vessel 64 between the distal end 36 of the insertion shaft 26 and the anchor 28 so that the needles, when advanced, pass through the vessel wall at a substantially perpendicular angle relative to the longitudinal movement of the needles 32.

Referring to FIGS. 5A and 5B, the second actuator 24 is operated to advance the needles through a wall of the vessel 64 and into contact with sutures 31 of the suture carrying portion 30. Referring to FIGS. 6A and 6B, the second actuator is operated to withdraw the needles 32 and place the sutures 31 across the wall of the vessel 64 adjacent to the vessel puncture 66. The first actuator 22 is also operated to retract the anchor 28 so that the suture placement device 12 may be withdrawn from the vessel 64. Prior to removing the suture placement device 12 from the vessel 64, the operator determines a depth of the tissue tract 62 by observing which of the first markings 38 is visible outside of the tissue layer 60. The suture placement device 12 is then removed from the vessel 64 and tissue tract 62 as shown in FIG. 7. The suture placement device 12 leaves behind the sutures 31 extending across the vessel puncture 66.

The suture locking device 14 includes a locking assembly 40, a carrier member 42, a handle 44, an actuator assembly 46, and snares 48. The carrier member 42 includes a distal end 50, a plurality of second markings 52, and a pair of snare apertures 54. The snares 48 include a loop end 56 positioned distal of the carrier member 42, and free ends 58 extending through the snare apertures 54.

The second markings 52 may be substantially the same in, for example, design, style, size, shape, etc. as the first markings 38. Providing the second markings 52 with similarities to, if not an exact copy of, the first markings 38 may make it easier for the operator to translate the depth information obtained by use of the suture placement device 12 to a target depth desired for the suture locking device 14 during operation.

In some arrangements, the second markings 52 may incorporate numerical markings or indices that take into account a length dimension of the locking assembly 40. For example, the first markings 38 may start with numerical indicators 1, 2, 3 starting at a distance of 1 mm from the distal end 36 of the insertion shaft 26, and the second markings 52 may start with numerical indicators 3, 4, 5 starting at 1 mm from the distal end 50 of the carrier member 42 to take into account the length of the locking assembly 40.

Details concerning operation of the suture locking device 14 are shown and described with reference to U.S. Patent Application No. 61/487,633, filed on 18 May 2011, and entitled "Suture Locking Device and Methods," which is incorporated herein in its entirety by this reference.

Figure 8C:
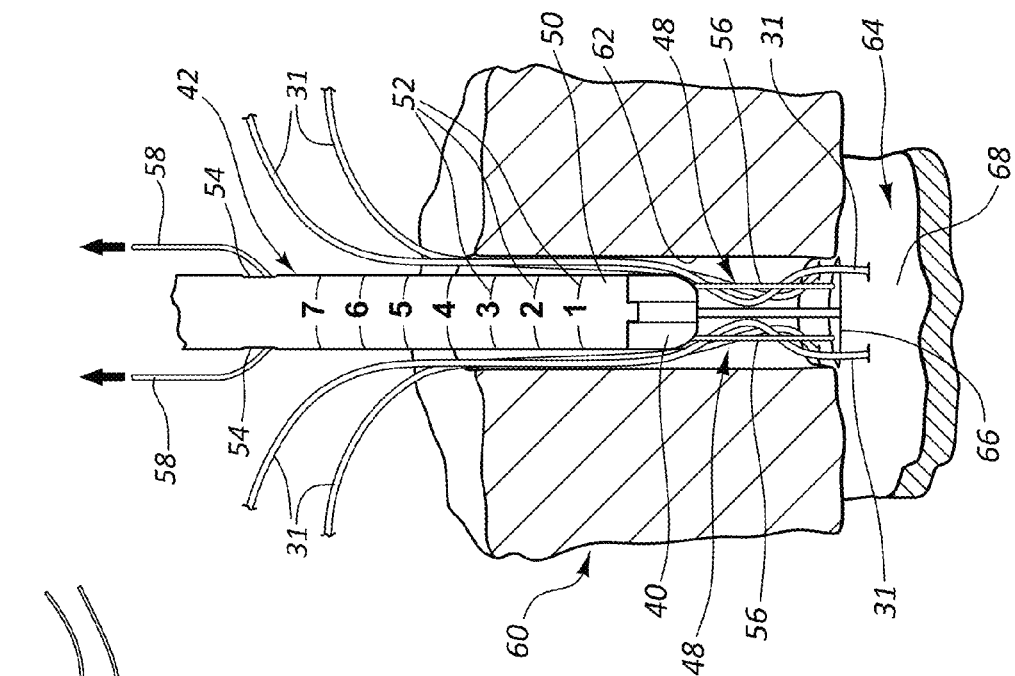
FIG. 8C shows the suture locking device of FIG. 1 from a top view and inserted into the tissue tract.
Figure 9:
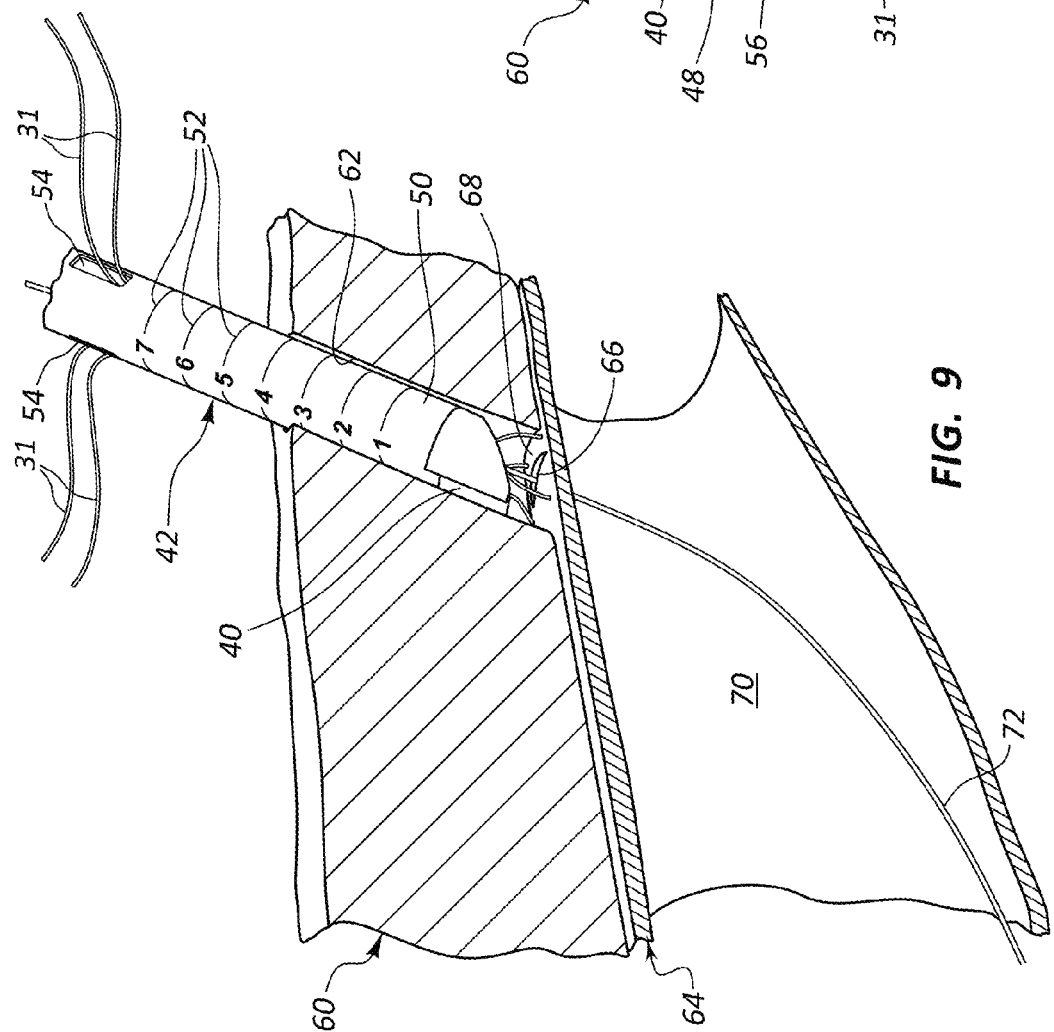
FIG. 9 shows the suture locking device of FIG. 8A with the snares withdrawn to position the sutures extending through a locking assembly.
Figure 10:
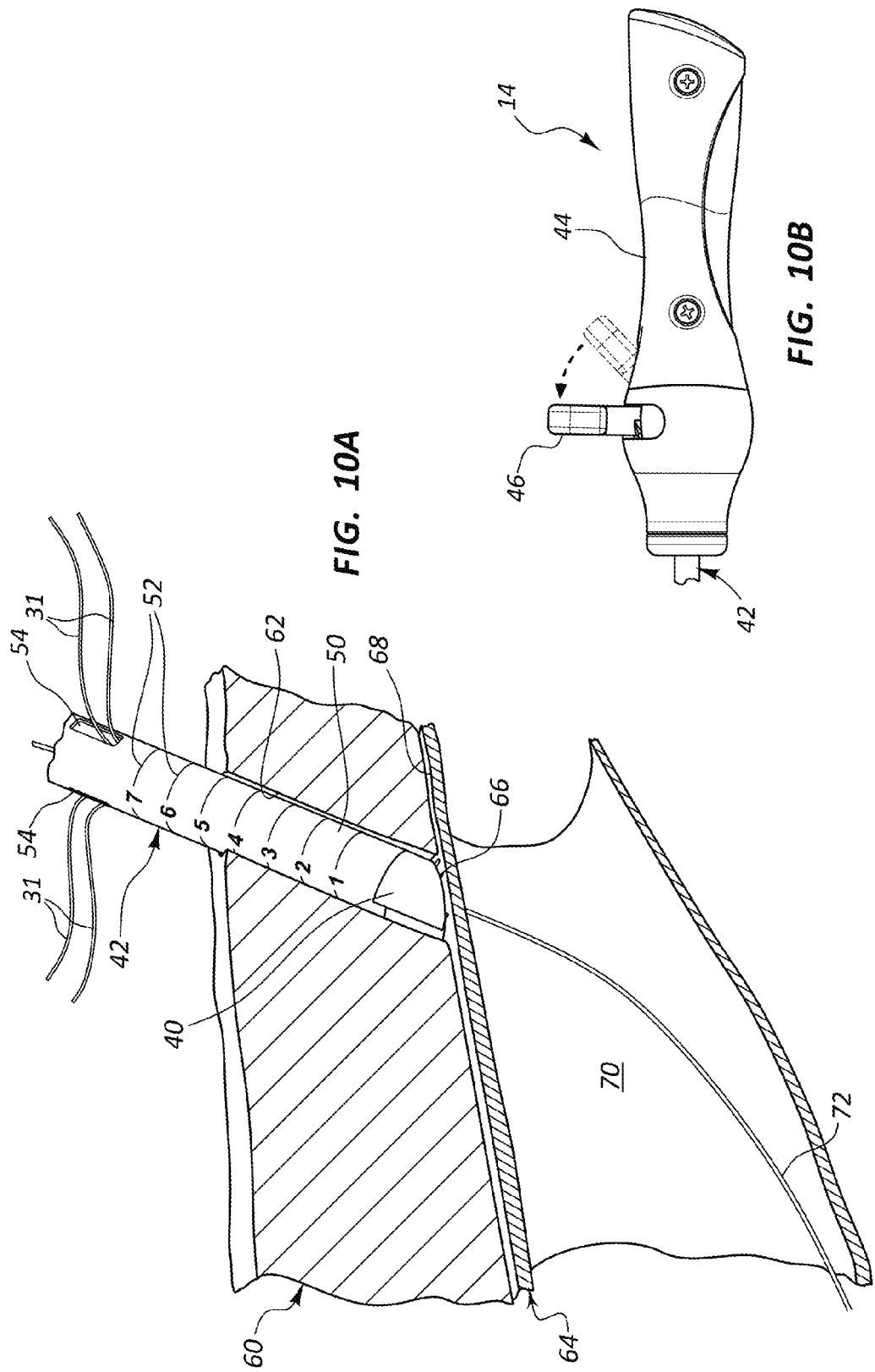
FIG. 10A shows the suture locking device of FIG. 9 advanced into contact with an outer surface of the vessel wall.
FIG. 10B shows the handle of the suture locking device of FIG. 10A in a second operation position.
Figure 11:
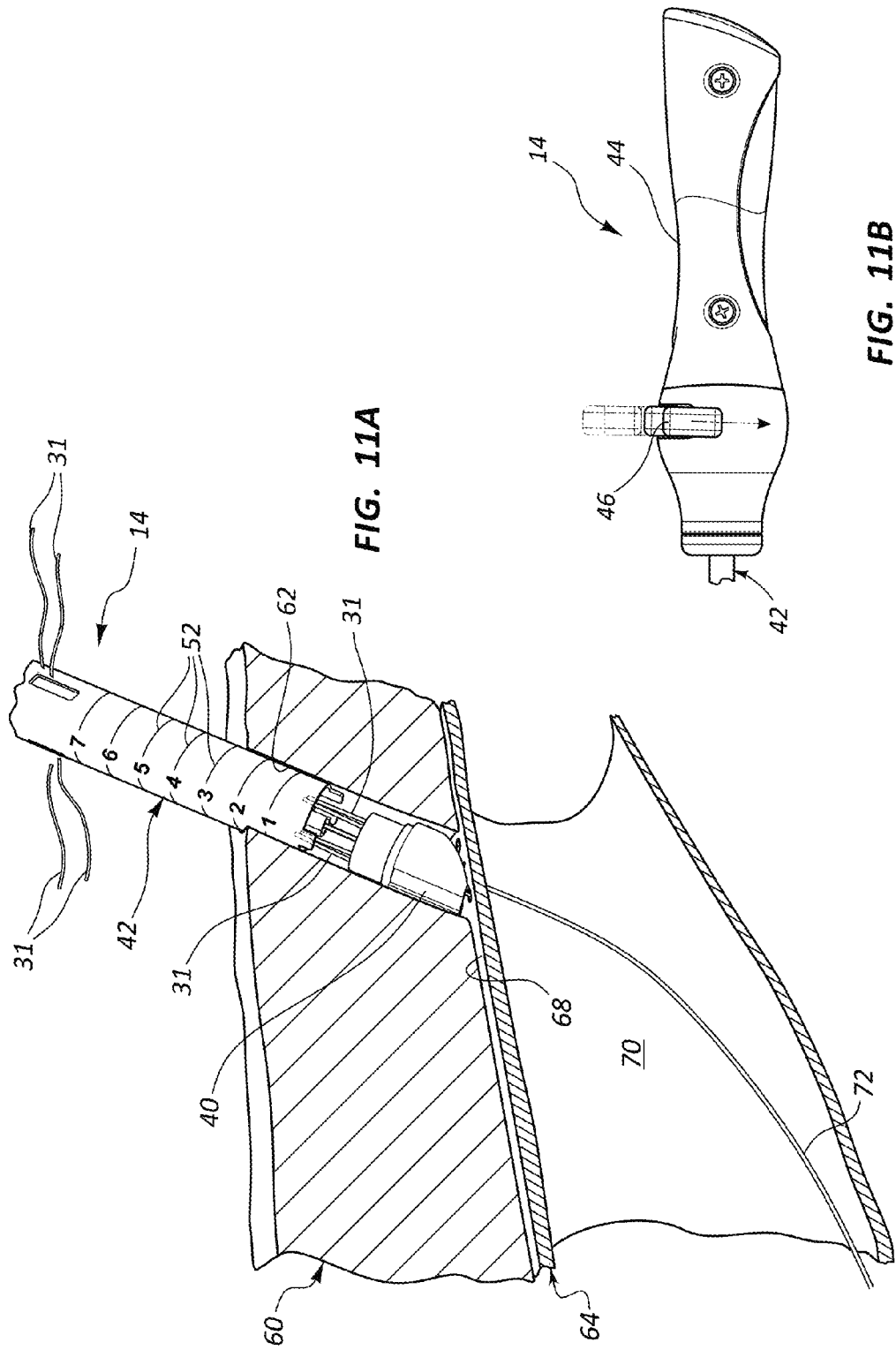
FIG. 11A shows the suture locking device of FIG. 10A operated to detach the locking assembly and cut the sutures.
FIG. 11B shows the handle of the suture locking device of FIG. 11A in a third operation position.

Operation of the suture locking device 14 is now described with reference to FIGS. 8A-12. Sutures 31, which have been placed across the vessel puncture 66 previously, may be routed through snares 48 at a location outside of the patient as shown in FIG. 8A. The sutures 31 may be drawn into the locking assembly 40 and carrier member 42 by pulling on the free ends 58 of the snares 48, as shown in FIGS. 8C and 9. The actuator assembly 46 may maintain a first operation position (see FIG. 8B), while routing the sutures 31 into the suture locking device 14. Tension is applied in the sutures 31 while advancing the suture locking device 14 to position the locking assembly 40 adjacent to the vessel puncture 66 in contact with the outer surface of the vessel 68, as shown in FIG. 10A. The operator may advance the carrier member 42 a depth into the tissue tract 62 as indicated by second markings 52 that corresponds to the depth of the tissue tract 62 determined in a prior procedure (e.g., using the suture placement device 12 as described above).

If the suture locking device 14 is not able to advance into the tissue tract 62 to a desired depth as indicated by the second markings 52, the operator may remove the carrier member 42 from the tissue tract 62 or make other positional adjustments to the suture locking device 14 in an attempt to reach the desired depth.

Figure 12:
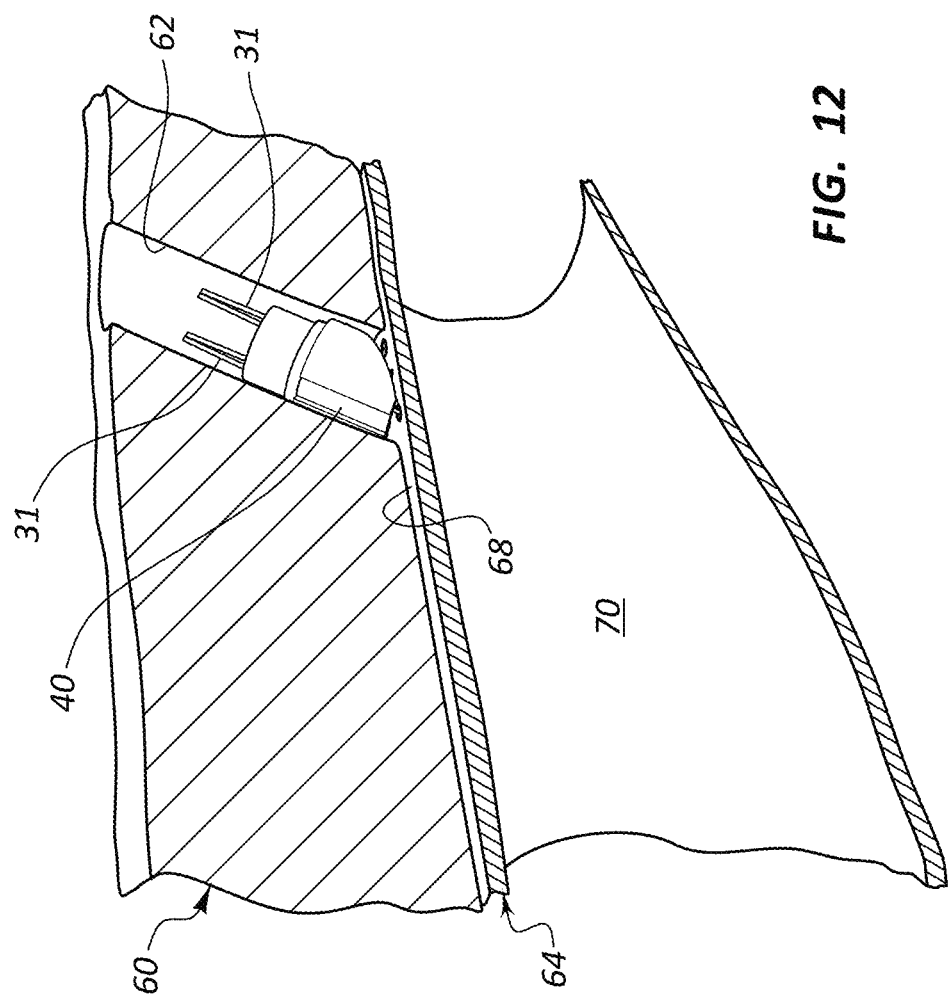
FIG. 12 shows the locking assembly of the suture locking device of FIG. 11A in position securing sutures across the vessel puncture.

Once the desired depth is achieved as indicated by second markings 52, the actuator assembly 46 is operated into a second operation position (see FIG. 10B) to lock the locking assembly 40 onto the sutures 31. Referring to FIG. 11A-B, the actuator assembly 46 is operated into a third operation position, as shown in FIG. 11B, to detach the locking assembly 40 from the carrier member 42. Operating the actuator assembly 46 into the third operation position may concurrently cut the sutures 31. The suture locking device 14 is then withdrawn to leave behind the locking assembly 40, as shown in FIG. 12. The locking assembly 40 may comprise a bioresorbable material that is absorbed by the body over time.

Referring now to FIG. 13A, an alternative marking pattern 80 is shown including a plurality of pattern portions 82A-G. Each of the pattern portions 82A-G may have a different design, color, texture, sheen, pattern, or other physical property or appearance that the operator observes to help determine a depth of a tissue tract. The marking pattern 80 may be positioned on any of the suture placement device 12, suture locking device 14, and other devices described above that may be part of a vascular closure system and are insertable into a tissue tract. The pattern portions 82A-G may comprise individual, circumferentially arranged rings. In some arrangements, the pattern portions 82A-G may be arranged at an angle that is typical of an angle of insertion of the device through a tissue tract to access the vessel puncture. FIG. 13B shows the pattern portions 82A-G arranged at an angle α relative to a longitudinal axis of the device. Typically, the angle α is in the range of about 30° to about 60°.

Figure 15:
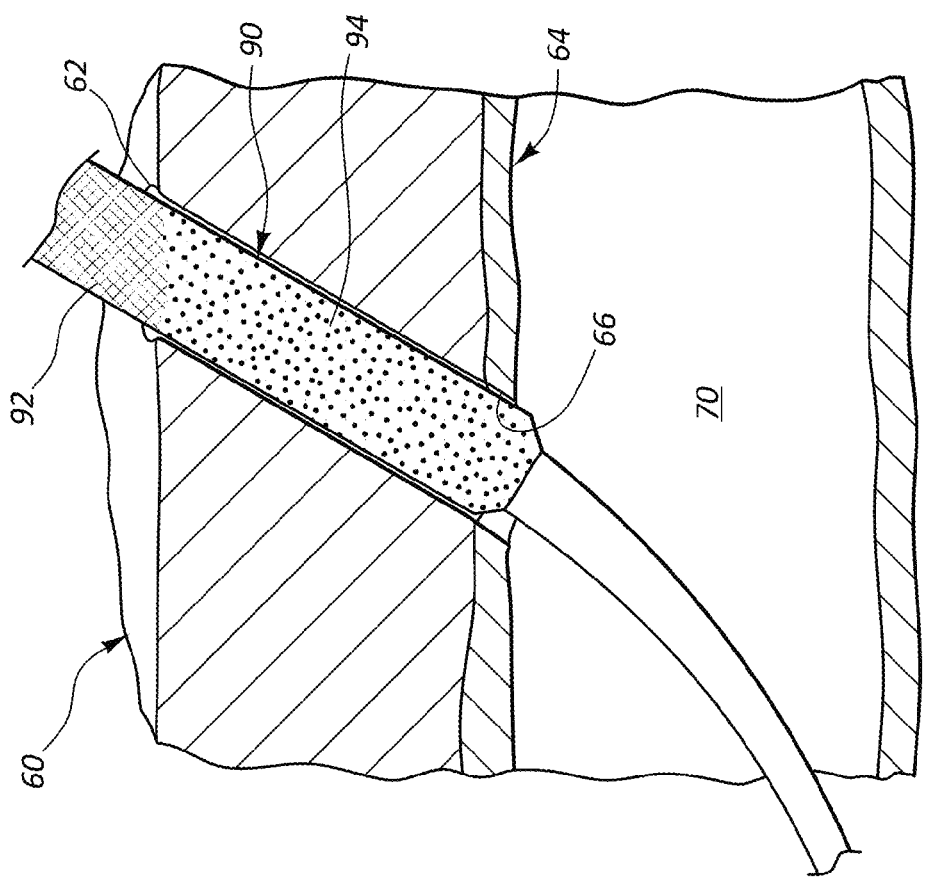
FIG. 15 shows the marking of FIG. 14 activated by contact with tissue in a tissue tract in accordance with the present disclosure.
Figure 14:
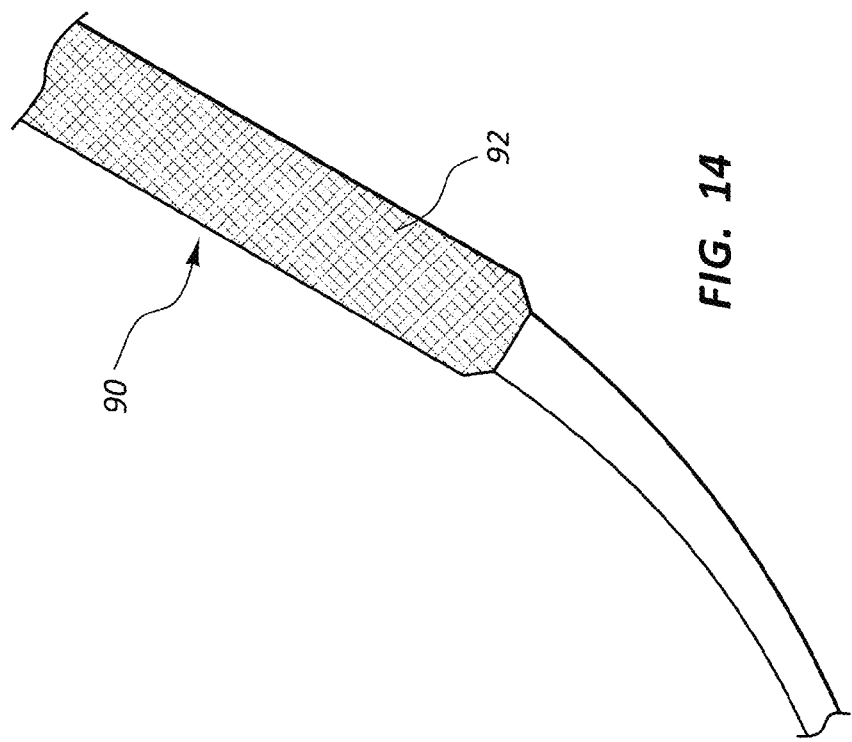
FIG. 14 shows an example marking for a vascular closure system.

Referring to FIGS. 14 and 15, at least one of the suture placement device 12, suture locking device 14, and other devices described above that may be part of a vascular closure system may include a marking surface 90. The marking surface 90 may include a first surface indicator 92 and a second surface indicator 94. The marking surface 90 may comprise surface features that change upon exposure of the device to the tissue or other substance within the tissue tract 62 to provide the first and second surface indicators 92, 94. For example, the first surface indicator 92 may be a first color that changes to the second surface indicator 94 upon contact of the marking surface 90 with the tissue defining the tissue tract 62 (see FIG. 15). In another arrangement, the first surface indicator 92 is a first sheen of the marking surface 90 that changes to a second, difference sheen (e.g., the second surface indicator 94) upon contact with tissue of the tissue tract 62 or another substance (e.g., blood) that is present within the tissue tract 62. In a still further example, the marking surface 90 comprises a heat-sensitive material that changes colors when heated by contact with the tissue tract 62 or material within the tissue tract 62.

Other embodiments may include a mechanical device that locks in a depth indication on one or both the suture placement device 12 and suture locking device 14. In one example, a mechanical device includes a collar or fastener that is manually positioned or activated by the operator at an axial location that indicates a depth of the tissue tract.

While the embodiments disclosed herein have been described with reference to determining a depth of a tissue tract that provides access to a puncture in a vessel accessible percutaneously through the tissue tract, similar principles may be applicable to determining depths for other reasons or at other locations. For example, the depth location may be used to determine a thickness of a vessel wall, an internal diameter of a vessel, an outer diameter of a vessel, or the like.

While this invention has been described with reference to certain specific embodiments and examples, it will be recognized by those skilled in the art that many variations are possible without departing from the scope and spirit of this invention. The invention, as defined by the claims, is intended to cover all changes and modifications of the invention which do not depart from the spirit of the invention.

What is claimed is:

1. A vascular closure assembly configured to seal a puncture in a vessel accessible through a tissue tract, comprising:
   a vascular closure device comprising:
      a handle assembly;
      an insertion shaft extending distally from the handle assembly and carrying a plurality of needles, the plurality of needles being operable to position at least one suture across the vessel puncture;
      an anchor assembly positioned distal of the insertion shaft;
      at least one suture member positioned distal of the insertion shaft;
      wherein the insertion shaft extends into the tissue tract to position the anchor assembly through the puncture and into the vessel, the insertion shaft including a first depth indicator on an outer surface thereof that indicates a depth of the tissue tract upon the first depth indicator contacting the tissue tract;
   at least one of a suture cutting device and a suture locking device, each of the suture cutting device and the suture locking device including a suture handle portion and a carrier member, the carrier member extending distally from the suture handle portion and into the tissue tract during operation, the carrier member including a second depth indicator on an outer surface thereof, the second depth indicator indicating the depth of the tissue tract upon the second depth indicator contacting the tissue tract.

2. The vascular closure assembly of claim 1, wherein the first and second depth indicators are identical.

3. The vascular closure assembly of claim 1, wherein the first and second depth indicators include a plurality of patterns.

4. The vascular closure assembly of claim 1, wherein the first and second depth indicators include a plurality of colors.

5. The vascular closure assembly of claim 1, wherein the first and second depth indicators include a plurality of indices.

6. The vascular closure assembly of claim 1, wherein the first depth indicator is activated by contact with the tissue tract.

7. The vascular closure assembly of claim 1, wherein the first depth indicator is actuated manually.

8. A method of closing a vessel puncture accessible through a tissue tract, comprising:
   providing a suture positioning device and a suture securing device, the suture positioning device comprising a first handle portion, an insertion member, and an anchor assembly, the suture securing device comprising a second handle portion and a carrier member;
   inserting the anchor assembly through the vessel puncture and the insertion member into the tissue tract;
   positioning at least one suture across the vessel puncture with the suture positioning device;
   providing a first visual indicator on the insertion member of a depth of the tissue tract;
   identifying a second visual indicator on the carrier member that represents the depth of the tissue tract;
   inserting the carrier member into the tissue tract to the depth after removing the suture positioning device from the tissue tract and while observing the second visual indicator.

9. The method of claim 8, wherein at least one of the first and second visual indicators includes at least one pattern.

10. The method of claim 8, wherein at least one of the first and second visual indicators includes a plurality of colors.

11. The method of claim 8, wherein the suture positioning device comprises a plurality of needles, the method further comprising advancing and retracting the plurality of needles to position the at least one suture across the vessel puncture.

12. The method of claim 8, wherein the suture securing device comprises a suture cutter configured to cut the at least one suture within the tissue tract.

13. The method of claim 8, wherein the suture securing device comprises a suture locking device configured to position a suture lock on the at least one suture to maintain tension in the at least one suture.

\* \* \* \* \*